United States Patent [19]

Rivetti et al.

[11] Patent Number: 5,705,673
[45] Date of Patent: Jan. 6, 1998

[54] CONTINUOUS PROCESS FOR THE PREPARATION OF PHENYL METHYL CARBONATE

[75] Inventors: Franco Rivetti, Milan; Renato Paludetto, Pioltello; Ugo Romano, Vimercate, all of Italy

[73] Assignee: Enichem S.p.A., Milan, Italy

[21] Appl. No.: 768,811

[22] Filed: Dec. 18, 1996

[30] Foreign Application Priority Data

Jan. 16, 1996 [IT] Italy ................... MI96A0056

[51] Int. Cl.⁶ ............................................. C07C 68/06
[52] U.S. Cl. ............................................. 558/270
[58] Field of Search ................................ 558/270

[56] References Cited

U.S. PATENT DOCUMENTS

| | | |
|---|---|---|
| 4,045,464 | 8/1977 | Romano et al. . |
| 4,182,726 | 1/1980 | Illuminati et al. . |
| 4,218,391 | 8/1980 | Romano et al. . |
| 5,210,268 | 5/1993 | Fukuoka et al. ................. 558/270 |
| 5,322,958 | 6/1994 | Dreoni et al. . |
| 5,344,954 | 9/1994 | Schön et al. .................. 558/270 X |
| 5,362,901 | 11/1994 | Wagner et al. ................. 558/270 |
| 5,380,908 | 1/1995 | Murata et al. .................. 558/270 |
| 5,395,949 | 3/1995 | Delledonne et al. . |

FOREIGN PATENT DOCUMENTS

| | | |
|---|---|---|
| 0 461 274 | 12/1991 | European Pat. Off. . |
| 0 591 923 | 4/1994 | European Pat. Off. . |

*Primary Examiner*—Michael G. Ambrose
*Attorney, Agent, or Firm*—Oblon, Spivak, McClelland, Maier & Neustadt, P.C.

[57] ABSTRACT

The present invention relates to a continuous process for the preparation of phenyl methyl carbonate. The process is carried out in a first distillation column consisting of a lower reactive section and an upper rectification section and a second rectification column. The reactive section of the first column has a practically constant thermal profile at the optimum temperature for the reaction, and that with the use of the second column a circulation of dimethyl carbonate is created between the top and bottom of the first column which allows an advantageous excess of dimethylcarbonate to be fed to the bottom of the first column.

23 Claims, 4 Drawing Sheets

5,705,673

CONTINUOUS PROCESS FOR THE PREPARATION OF PHENYL METHYL CARBONATE

BACKGROUND OF THE INVENTION

1. Field of the Invention

The present invention relates to a continuous process for the preparation of phenyl methyl carbonate with high productivity values.

2. Description of the Background

The preparation of aromatic esters of carbonic acid starting from aliphatic esters of carbonic acid and phenol, is known in the art. In particular, the preparation of phenyl methyl carbonate and diphenyl carbonate is known.

The aromatic esters of carbonic acid are useful as intermediates in the chemical industry. For example, they are used in the production of aromatic polycarbonates, isocyanates, urethanes and ureas. They are therefore of great industrial and commercial interest.

The transesterification reaction between phenols and dialkylcarbonates to give the corresponding aryl alkyl and diarylcarbonates is an equilibrium reaction and is carried out in the presence of a catalyst. Among the numerous examples of catalysts provided in the art, those based on titanium described in German patent 2528412 have proved to be particularly effective.

The known art also discloses that equilibrium reactions can be conveniently carried out in reactors equipped with an overlying distillation column or in reactive distillation columns, in order to shift the equilibrium towards the formation of the product.

In fact, in most cases of equilibrium reactions, as also in the case under subject, one of the products is more volatile than the other components of the reaction system and can therefore be easily removed.

Processes of this type, in the case of the preparation of aromatic carbonic esters, are described for example in German patent 3445552 and patents EP 89709 and EP 461274.

In the above cases however, industrial exploitation of the invention is made difficult by the equilibrium constant of the reaction which, being extremely low, is such that the reaction is almost completely shifted in the direction of aliphatic carbonate.

The problem can be solved by preparing the diaryl carbonate by the disproportionation reaction of alkyaryl carbonates, according to the following equation:

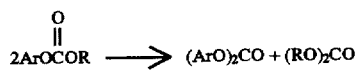

This reaction, described in U.S. Pat. No. 4,045,464, is in fact more easily effected.

SUMMARY OF THE INVENTION

It is necessary however to have a process for the preparation of alkyl aryl carbonate starting from an aliphatic carbonate which enables significant conversions and productivies to be obtained, on an industrial scale, with the minimum waste of energy.

It has now been found that alkyl aryl carbonate can be prepared with particularly significant conversions and productivities from an industrial view point and with a minimum energy waste, operating according to the conditions described in the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
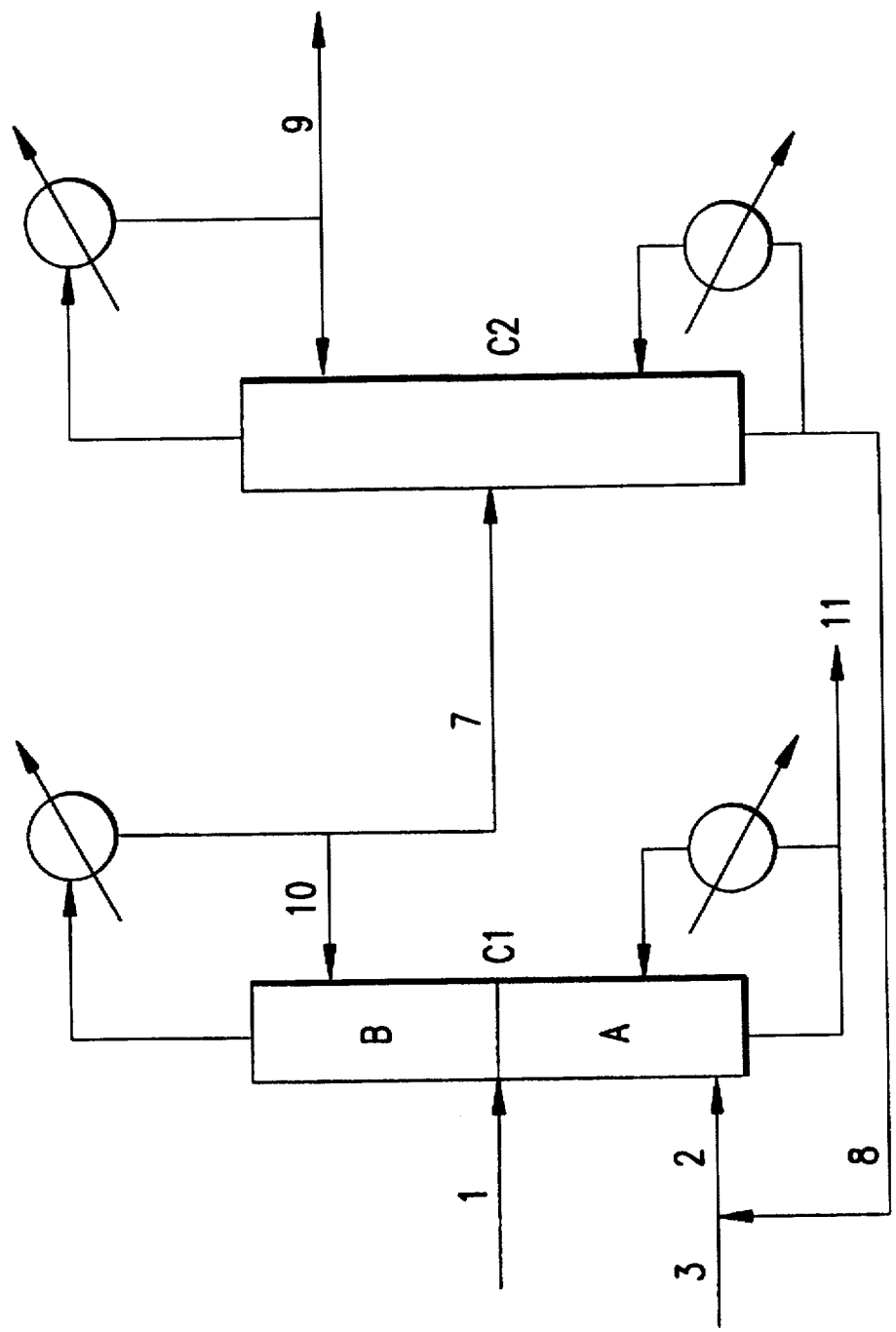
FIG. 1 is a diagram of a distillation embodiment of the invention for the preparation of an alkyl aryl carbonate.

In practice, the invention requires that the process be carried out in a first distillation column consisting of a lower reactive section and an upper rectification section and a second rectification column, under such operating conditions that the reactive section of the first column has a practically constant thermal profile at the optimum temperature for the reaction and that with the use of the second column a circulation of dimethyl carbonate is created between the top and bottom of the first column which allows an advantageous excess of dimethylcarbonate to be fed to the bottom of the first column. The latter not only acting as reagent, but also as stripping agent, allows the concentration of methanol on the bottom of the column to be reduced thus favouring the conversion.

In its widest aspect the invention relates to a continuous process for the preparation of phenyl methyl carbonate starting from phenol, dimethyl carbonate and a transesterification catalyst, which comprises:

(a) carrying out the process in a first distillation column consisting of a lower reactive section and an upper rectification section and in a second rectification column;

(b) feeding to the top of the reaction section of the first column a stream (I) containing phenol and optionally dimethylcarbonate in a ratio equal to or higher than 60/40 by weight and all of the catalyst;

feeding to the bottom of the reactive section of the same column a stream (II), comprising a stream or part of a stream (III) extracted from the bottom of the second column, containing dimethylcarbonate and optionally phenol in a ratio equal to or higher than 80/20 by weight;

the streams (I) and (II) being fed in such a quantity that the ratio between the total moles of dimethylcarbonate and phenol fed is between 2:1 and 10:1, preferably between 3:1 and 6:1;

feeding to the top of the rectification section of the first column a stream (IV) which consists of the reflux of the column, having the composition of a stream (V) taken from the top of the column itself and fed to the second column, in such a quantity that the weight ratio between the refluxed liquid and the distillate i.e. between stream IV and stream V, is within the range of 0.2–0.8.

c) extracting from the bottom of the reactive section of the first column a stream (VI) essentially containing all the non-reacted phenol, the phenyl methyl carbonate and any possible diphenylcarbonate produced, the transesterification catalyst and a fraction of the dimethyl carbonate fed so that the molar ratio in this stream between the dimethylcarbonate and the phenol is between 0.5 and 5, preferably between 1 and 5;

extracting from the top of the rectification section of the first column, a stream V, essentially containing dimethylcarbonate and all or basically all of the methanol produced by the reaction;

d) feeding to an intermediate section of the second column a stream (V) extracted from the top of the first column;

e) extracting from the top of the second column a stream (VII) containing all or practically all of the methanol fed to the second column and containing methanol and dimethyl carbonate in a ratio of more than 50% by weight;

extracting from the bottom of the second column a stream (III) essentially consisting of the remaining dimethylcarbonate;

f) recycling said stream III or part of it to the bottom of the first column.

FIG. 1 of the enclosed drawing schematically shows an apparatus suitable for the embodiment of the process of the present invention.

In particular C1 is a reactive distillation column consisting of a lower section A in which the reactive distillation takes place and an upper rectification section B.

The reactive distillation section A of the column comprises at least 3 theoretical steps, but normally comprises from 5 to 25 theoretical distillation steps, carried out by distillation plates or by packed columns well known in the art.

Rectification section B comprises at least 3 theoretical steps, but normally comprises from 5 to 25 theoretical distillation steps, carried out by distillation plates or by packed columns well known in the art.

The stream 1 is a stream mainly containing phenol and optionally dimethyl carbonate, rich in phenol, meaning that it contains phenol and DMC in a ratio equal to or higher than 60/40 by weight.

The phenol and dimethylcarbonate contained in stream 1, can either be fresh or recycled reagents, coming from the downstream sections of the plant.

In addition stream 1 contains all the catalyst, either fresh or possibly recycled, coming from the downstream sections of the plant.

The reactive section of the distillation column C1 is also fed to the bottom by stream 2, mainly containing dimethyl carbonate and optionally phenol in a ratio equal to or higher than 80/20 by weight. The dimethylcarbonate and phenol contained in this stream can either be fresh or recycled reagents, coming from the downstreem sections of the plant. In particular, with reference to FIG. 1, at least a part of the dimethyl carbonate comes from the bottom of the column C2 (stream 8).

Streams 1 and 2 are fed in such a quantity that the ratio between the total moles of dimethylcarbonate and phenol fed to C1 is between 2:1 and 10:1, this ratio is normally between 3:1 and 6:1.

Stream 10, is also fed to the top of the rectification section B of the column C1 and forms the reflux to the column itself. This stream 10 as illustrated in FIG. 1 has the composition of stream 7 taken from the top of the column itself essentially containing dimethylcarbonate and methanol.

Stream 10 is fed to the column C1 in such a quantity that the reflux ratio obtained, i.e. the weight ratio between stream 10 and stream 7 is within the range of 0.2–0.8.

Stream 7 taken from the top of the column C1 essentially consists of dimethylcarbonate and all or practically all of the methanol produced in the reaction.

It may also contain phenol but the content of phenol is normally as little as possible, for example less than 1 or 2% by weight. The concentration of methanol in this stream is usually between 1 and 5% by weight. Stream 7 is sent to the feeding of column C2.

A stream 11 essentially containing all the non-reacted phenol, phenyl methyl carbonate and any possible diphenyl carbonate produced, the transesterification catalyst and a fraction of the dimethylcarbonate fed, is extracted from the bottom of the reaction section of column C1 so that the molar ratio, in this stream, between the dimethyl carbonate and the phenol is between 0.5 and 5, normally between 1.0 and 5.0. This fraction usually forms between about 10 and about 60% of the total dimethyl carbonate fed to column C1.

Figure 2:
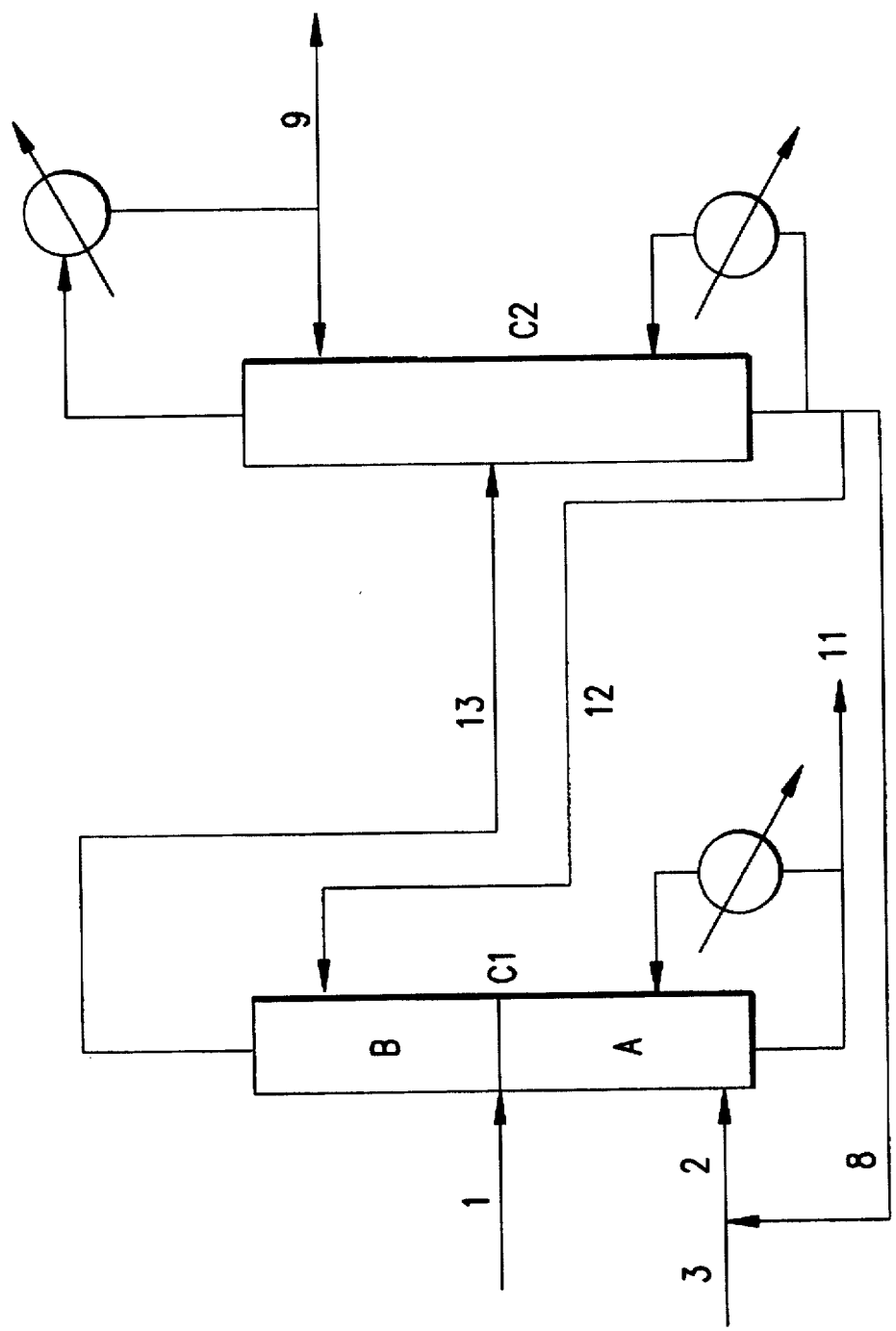
FIG. 2 is a diagram of an alternative distillation apparatus for the preparation of an alkyl aryl carbonate.

An alternative embodiment of the process of the invention is illustrated in the arrangement of FIG. 2.

In this case a stream 13 taken from the top of column C1 is fed to the intermediate section of column C2 whereas a stream 12, separated from stream 8 taken from the bottom of column C2, essentially containing dimethylcarbonate, is fed as reflux to column C1.

Stream 12 is fed to column C1 in such a quantity that the reflux ratio which is obtained, i.e. the weight ratio between stream 12 and the difference 13–12 is within the range of 0.2–0.8.

The operating pressure of the column C1, measured at the top of the column, is generally between 3 and 10 absolute bars, normally between 4 and 8 absolute bars. The temperature at the bottom of the reaction section of column C1 is generally maintained at between 250° and 150° C., normally between 220° and 180° C. Operating according to the invention the reactive section A of column C1 is substantially isothermal, in the sense that there is generally a difference of not more than 20° C. between the temperature at the bottom and that of the feeding zone of stream 1.

The temperature measured at the top of column C1 is generally between 110° and 210° C., normally between 140° and 180° C.

Column C2 is a rectification column containing at least 10 theoretical steps, normally from 20 to 50 theoretical distillation steps, carried out by means of distillation plates or by packed columns well known in the art. It is fed into its intermediate section, at a height generally selected so that the theoretical steps present above and below the feeding are in a ratio of between 1/3 and 3/1, normally between 1/1 and 1/3, with the stream coming from the top of column C1.

Column 2 separates from the top a stream 9 containing all or practically all of the methanol fed and rich in methanol, in the sense that it contains methanol and dimethylcarbonate in a ratio of more than 1/1 by weight, and also containing dimethylcarbonate. This stream 9 can be conveniently recirculated to a plant for the production of dimethylcarbonate.

Column C2 separates from the bottom a stream 8 essentially consisting of residual dimethylcarbonate, i.e. not taken from the top, as well as possible small quantities of phenol present in stream 7. This stream 8, or part of it, is recycled to the bottom of C1.

The operating conditions of column C2 are not particularly critical; it conveniently operates with a pressure, measured at the top, of between 1 and 10 absolute bars, and with temperatures at the top and bottom of between 65° and 135° C. and between 90° and 180° C. respectively.

The process of the invention is conveniently carried out in the presence of a catalyst selected from those known in the art, preferably homogeneous, i.e. soluble in the reaction medium and basically not volatile. The catalysts described in German patent 2528412 already cited have proved to be particularly useful and among these alkoxides and aryl oxides of titanium, in particular titanium tetraphenate, conveniently used in a concentration, with respect to the total phenol fed, of between 0.1 and 10% in moles, normally between 0.2 and 2% in moles.

Operating in the presence of these catalysts the reaction, under the conditions described, takes place with a high rate and selectivity, the latter generally being more than 99% molar with respect to the phenol and dimethylcarbonate and normally more than 99.5%.

Although these values are extremely high, small quantities of by-products however, mainly anisole, are formed during the reaction and can be left to accumulate in the process streams without any particular counter-effects as they behave as inert components for the purposes of the process. For example the anisole can be left to accumulate in the process streams up to values of even 20–30% by weight and maintained at these concentrations by means of appropriate flushing operations of the process fluids.

Figure 3:
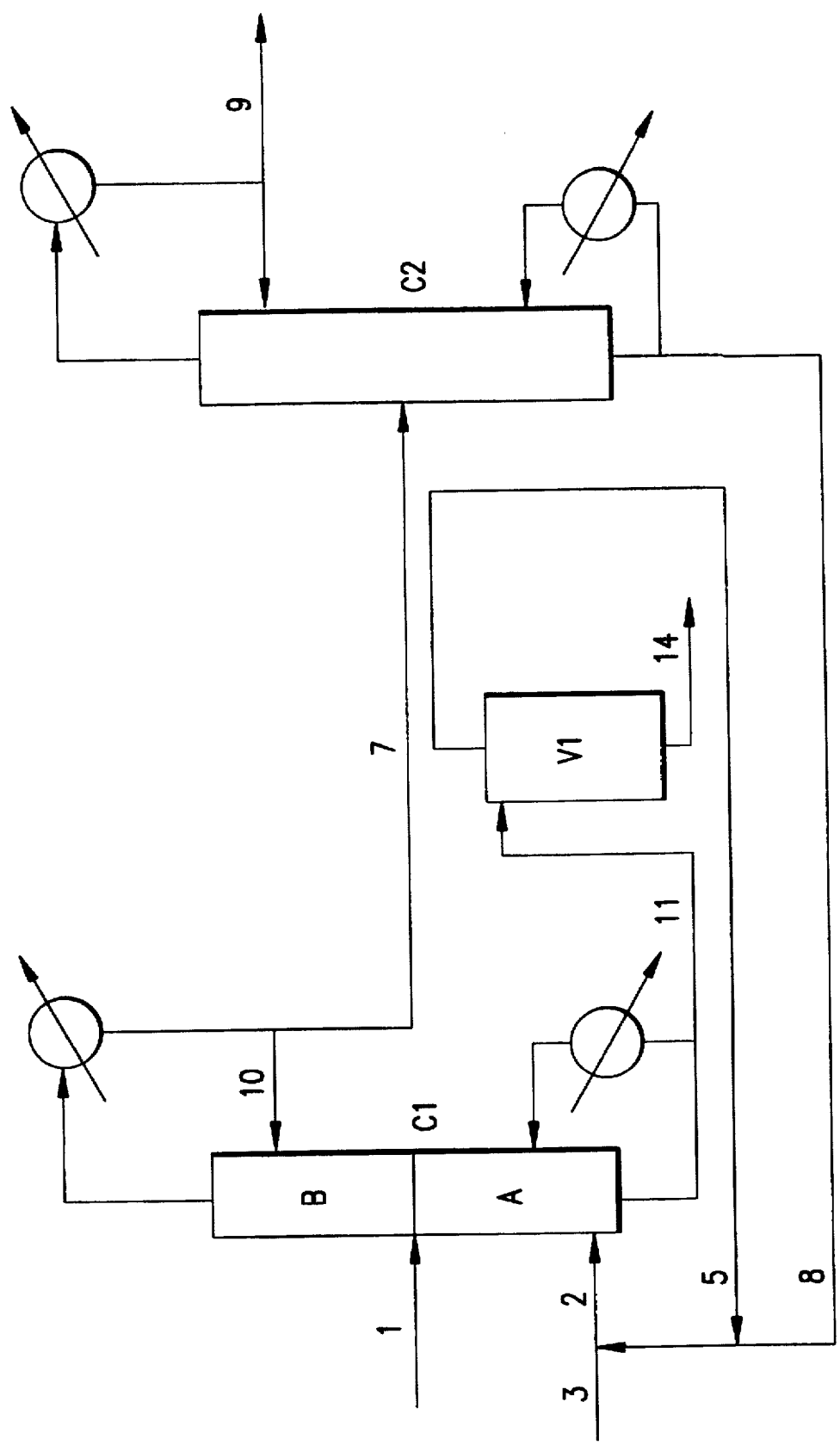
FIG. 3 is a diagram of a modification of the distillation apparatus of FIG. 1.
Figure 4:
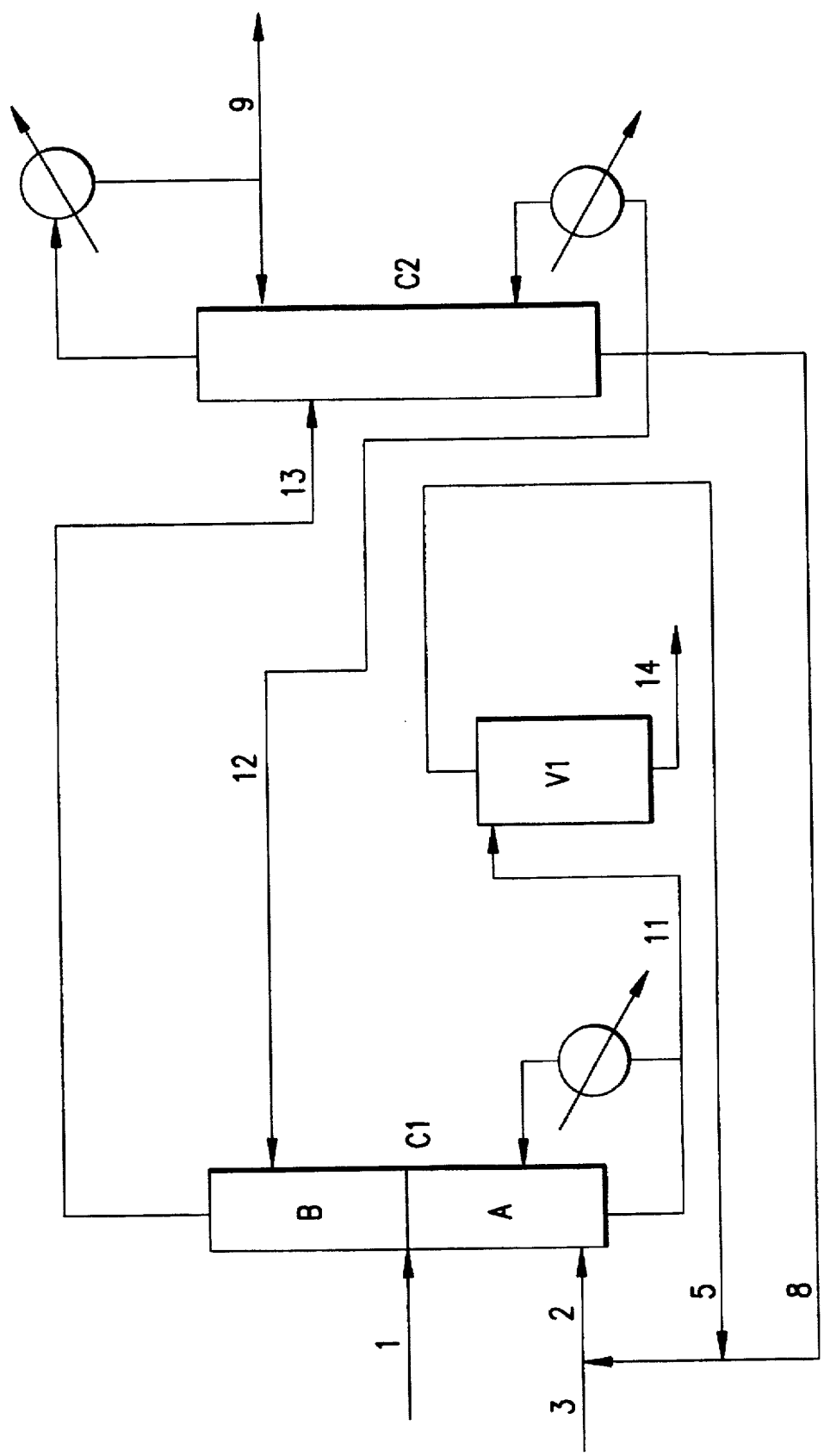
FIG. 4 is a modification of the distillation apparatus of FIG. 3.

In one form of embodiment the stream 11 coming from the bottom of column C1 is subjected to adiabatic flash by pressure reduction, using the arrangement illustrated in FIG. 3 and FIG. 4. With reference to the figures, the stream 11 is subjected to adiabatic flash in the flash chamber V1, operating at a pressure lower than the operating pressure of column C1, normally at atmospheric pressure. When V1 operates at atmospheric pressure, the flash temperature is generally between 120° and 170° C. In this way, a vaporized stream 5 is obtained at the head normally in a quantity equal to a weight fraction of the feeding to V1 of between 20 and 40%, rich in dimethyl carbonate, this meaning that it generally contains a ratio dimethyl carbonate/phenol equal to or higher than 80/20 by weight, and also containing phenol and small quantities of the product. This stream 5 is fed to the bottom of the reactive section of column C1 to form, together with stream 8 previously described coming from the bottom of column C2, stream 2 rich in dimethyl carbonate.

The stream taken from the bottom of the flash chamber, stream 14, is rich in phenol, in the sense that it contains a ratio phenol/dimethylcarbonate which is higher than that present in the stream fed. It also contains most of the product formed, as well as all of the catalyst.

This stream, as also stream 11, can be conveniently sent to the disproporation reaction to obtain diphenyl carbonate, as described in the above U.S. Pat. No. 4,045,464.

Alternatively, the phenyl methyl carbonate can be separated from the above streams 11 or 14 by the well known conventional techniques and subsequently subjected to disproportionation to obtain diphenyl carbonate.

Streams 11 or 14 normally contain the phenylmethyl carbonate produced in a concentration of between 10 and 40%.

A further object of the present invention therefore relates to a continuous process for the preparation of phenylmethyl carbonate as described above, also characterized in that stream 11 extracted from the bottom of the reactive section of column C1 is subjected to adiabatic flash by pressure reduction in a flash chamber and the vaporized stream thus obtained extracted from the top of the flash chamber, is fed to the bottom of the reactive section of column C1.

Operating in accordance with the invention described so far productivities of diphenyl carbonate of about 500 g/l hr are obtained, useful reaction volume meaning the sum of the hold-up volumes of the bottom and plates (or of the free space in the filling zone) of the reactive section of column C1, together with conversions per passage of phenol of about 25–35% with selectivities of about 99.5% with respect to the phenol and dimethylcarbonate, and an energy consumption of about 900 Kcal per Kg of-phenylmethylcarbonate produced, as can be seen in the following examples.

Example Nr. 1

With reference to FIG. 1, $C_1$ is a stainless steel distillation column with a diameter of 120 mm and height of 4 m, containing 40 perforated plates, with a distance between each plate of 100 mm and hold-up of each single plate equal to about 400 $cm^3$ of liquid. The heat is supplied at the bottom of the column by a circulation reboiler and the hold-up of the bottom and reboiler is 1000 $cm^3$.

The 40 perforated plates of which 15 are in the non-reactive section B and 25 in the reactive section A have an overall efficiency corresponding to 25 theoretical steps.

$C_2$ is a stainless steel column with a diameter of 120 mm and height of 6 m, containing 60 perforated plates with a distance between each plate of 100 mm, and overall efficiency corresponding to about 40 theoretical steps. $C_2$ is fed to the 40th plate from the bottom.

Column $C_1$ operates at a temperature at the bottom of 205° C. and at the top of 162° C., with pressures, measured at the top and bottom of the column, equal to 7.8 and 8.8 absolute bars respectively, and with a reflux ratio, measured as a ratio of the hourly flow-rates of streams 10 and 7, equal to 0.65.

Column $C_2$ operates at a temperature at the bottom of 130° C. and at the top of 95° C., with a pressure measured at the top of the column of 3 absolute bars and with a reflux ratio (liquid/distillate) equal to 4.6.

The catalyst, titanium tetraphenate, is fed together with the phenol in stream 1 in a quantity equal to 0.2 Kg/hr (0.5% molar of the phenol fed), and is extracted together with stream 11.

Table 1 shows the main components and hourly flow-rates under steady conditions of the streams.

The conversion % of the phenol obtained, the production and specific energy consumption (Kcal/Kg PMC produced) measured at the reboiler of column $C_1$, are also indicated.

Example Nr. 2

With reference to FIG. 3, $C_1$ and $C_2$ are distillation columns as described in example 1.

V1 is a stainless steel adiabatic flash chamber, with a diameter of 150 mm and height of 400 mm.

Column $C_1$ operates at a temperature at the bottom of 205° C. and at the top of 170° C., with pressures, measured at the top and bottom of the column, equal to 7.8 and 8.8 absolute bars respectively, and with a reflux ratio, measured as a ratio of the hourly flow-rates of streams 10 and 7, equal to 0.56.

Column $C_2$ operates as in example 1. V1 operates an adiabatic flash at atmospheric pressure and at a temperature of 125° C.

The catalyst, Titanium tetraphenate, is fed together with the phenol in stream 1, in a quantity equal to 0.2 Kg/hr (0.5% molar of the phenol fed), and is extracted together with stream 14.

Table 2 shows the main components and hourly flow-rates under steady conditions of the single streams. The conversion % of phenol, the production obtained and specific energy consumption (Kcal/Kg PMC produced) measured at the reboiler of column $C_1$, are also indicated.

Example Nr. 3

With reference to FIG. 3, $C_1$, $C_2$ and V1 are distillation columns and an adiabatic flash chamber as described in example 2.

Column $C_1$ operates at a temperature at the bottom of 205° C. and at the top of 163° C., with pressures, measured at the top and bottom of the column, equal to 7.8 and 8.8 absolute bars respectively, and with a reflux ratio, measured as a ratio of the hourly flow-rates of streams 10 and 7, equal to 0.42.

Column $C_2$ operates as in example 1. V1 operates an adiabatic flash at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 3 shows the main components and hourly flow-rates under steady conditions of the single streams. The conversion % of phenol, the production obtained and specific energy consumption (Kcal/Kg PMC produced) measured at the reboiler of column $C_1$, are also indicated.

Example Nr. 4 (comparative)

With reference to FIG. 3, $C_1$, $C_2$ and V1 are distillation columns and an adiabatic flash chamber as described in example 2.

Column $C_1$ operates at a temperature at the bottom of 205° C. and at the top of 165° C., with pressures, measured at the top and bottom of the column, equal to 7.8 and 8.8 absolute bars respectively, and with a reflux ratio, measured as a ratio of the hourly flow-rates of streams 10 and 7, equal to 0.41.

Column $C_2$ operates as in example 1. V1 operates an adiabatic flash of the stream 11 fed, at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 4 shows the main components and hourly flow-rates under steady conditions of the single streams. The conversion % of phenol, the production obtained and specific energy consumption (Kcal/Kg PMC produced) measured at the reboiler of column $C_1$, are also indicated.

This example if compared with examples 2 and 3 shows that when operating outside the scope of the invention as far as the composition of stream 1 is concerned, there is a considerable reduction in the conversion of the phenol and an increase in energy consumption.

Example Nr. 5 (comparative)

With reference to FIG. 3, $C_1$, $C_2$ and V1 are distillation columns and an adiabatic flash chamber as described in example 2.

Column $C_1$ operated at a temperature at the bottom of 205° C. and at the top of 192° C., with pressures, measured at the top and bottom of the column, equal to 7.8 and 8.8 absolute bars respectively, and with a reflux ratio, measured as a ratio of the hourly flow-rates of streams 10 and 7, equal to 0.13.

Column $C_2$ operates as in example 1. V1 operates an adiabatic flash of the stream 11 fed, at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 5 shows the main components and hourly flow-rates under steady conditions of the single streams. The conversion % of phenol, the production obtained and specific energy consumption (Kal/Kg PMC produced) measured at the reboiler of column $C_1$, are also indicated.

This example if compared with examples 2 and 3 shows that when operating outside the scope of the invention as far as the reflux ratio is concerned, there is a considerable reduction in the conversion of the phenol and an increase in energy consumption.

Example Nr. 6 (comparative)

With reference to FIG. 3, $C_1$, $C_2$ and V1 are distillation columns and an adiabatic flash chamber as described in example 2.

Column $C_1$ operates at a temperature at the bottom of 205° C. and at the top of 163° C., with pressures, measured at the top and bottom of the column, equal to 7.8 and 8.8 absolute bars respectively, and with a reflux ratio, measured as a ratio of the hourly flow-rates of streams 10 and 7, equal to 1.25.

Column $C_2$ operates as in example 1. V1 operates an adiabatic flash of the stream 11 fed, at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 6 shows the main components and hourly flow-rates under steady conditions of the single streams. The conversion % of phenol, the production obtained and specific energy consumption (Kcal/Kg PMC produced) measured at the reboiler of column $C_1$, are also indicated.

This example if compared with examples 2 and 3 shows that when operating outside the scope of the invention as far as the reflux ratio at the top of column $C_1$ is concerned, there is a considerable reduction in the conversion of the phenol and an increase in energy consumption.

Example Nr. 7

With reference to FIG. 4, $C_1$, $C_2$ and V1 are distillation columns and an adiabatic flash chamber as described in example 2.

Column $C_1$ operates at a temperature at the bottom of 205° C. and at the top of 165° C., with pressures, measured at the top and bottom of the column, equal to 7.8 and 8.8 absolute bars respectively, and with a reflux ratio, measured as a ratio between the hourly flow-rate of stream 12 and the difference between the hourly flow-rates of streams 13 and 12 (i.e. the net distillate), equal to 0.50.

Column $C_2$ operates as in example 1. V1 operates an adiabatic flash of the stream 11 fed, at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 7 shows the main components and hourly flow-rates under steady conditions of the single streams. The conversion % of phenol, the production obtained and specific energy consumption (Kcal/Kg PMC produced) measured at the reboiler of column $C_1$, are also indicated.

Example Nr. 8 (comparative)

With reference to FIG. 4, $C_1$, $C_1$ and V1 are distillation columns and an adiabatic flash chamber as described in example 2.

Column $C_1$ operates at a temperature at the bottom of 205° C. and at the top of 168° C., with pressures, measured at the top and bottom of the column, equal to 7.8 and 8.8 absolute bars respectively, and with a reflux ratio, measured as a ratio between the hourly flow-rate of stream 12 and the difference between the hourly flow-rates of streams 13 and 12 (i.e. the net distillate), equal to 3.0.

Column $C_2$ operates as in example 1. V1 operates an adiabatic flash of the stream 11 fed, at atmospheric pressure and at a temperature of 125° C.

The catalyst, Titanium tetraphenate, is fed together with stream 1, in a quantity equal to 0.2 Kg/hr (0.5% molar of the phenol fed), and is extracted together with stream 14.

Table 8 shows the main components and hourly flow-rates under steady conditions of the single streams. The conversion % of phenol, the production obtained and specific energy consumption (Kcal/Kg PMC produced) measured at the reboiler of column $C_1$, are also indicated.

This example if compared with example 7 shows that when operating outside the scope of the invention as far as the reflux ratio is concerned, there is no improvement in the conversion of the phenol whereas there is a considerable increase in energy consumption.

TABLE 1

| Stream Nr. | 1 | 2 | 3 | 7 | 8 | 9 | 10 | 11 |
|---|---|---|---|---|---|---|---|---|
| Kg/hr | 8.8 | 43.3 | 25.9 | 19.0 | 17.4 | 1.6 | 12.3 | 33.2 |
| % weight | | | | | | | | |
| $CH_3OH$ | | | | 5.5 | | 64.5 | 5.5 | |
| DMC | | 100 | 100 | 94.5 | 100 | 35.5 | 94.5 | 67.6 |
| Phenol | 100 | | | | | | | 17.3 |
| PMC | | | | | | | | 15.1 |

Conversion of phenol = 35%
(streams 1.11)
Production PMC = 5.0 Kg/hr
Specific energy consumption = 890 Kcal/Kg product

TABLE 2

| Stream | 1 | 2 | 3 | 5 | 7 | 8 | 9 | 10 | 11 | 14 |
|---|---|---|---|---|---|---|---|---|---|---|
| Kg/hr | 8.8 | 44.4 | 15.1 | 13.5 | 17.4 | 15.8 | 1.6 | 9.8 | 35.8 | 22.4 |
| % weight | | | | | | | | | | |
| $CH_3OH$ | | | | | 5.9 | | 64.5 | 5.9 | | |
| DMC | | 97.5 | 100 | 93.3 | 92.8 | 98.6 | 35.5 | 92.8 | 67.6 | 52.1 |
| Phenol | 100 | 1.8 | | 4.3 | 1.3 | 1.4 | | 1.3 | 17.9 | 26.1 |
| PMC | | 0.7 | | 2.3 | | | | | 14.5 | 21.8 |

Conversion of phenol = 34%
(streams 1.14)
Production PMC = 4.9 Kg/hr
Specific energy consumption = 870 Kcal/Kg product

TABLE 3

| Stream | 1 | 2 | 3 | 5 | 7 | 8 | 9 | 10 | 11 | 14 |
|---|---|---|---|---|---|---|---|---|---|---|
| Kg/hr | 13.5 | 39.5 | 9.9 | 13.3 | 17.7 | 16.3 | 1.4 | 7.4 | 35.3 | 22.0 |
| % weight | | | | | | | | | | |
| $CH_3OH$ | | | | | | | 64.5 | | | |
| DMC | 34.6 | 97.7 | 100 | 93.3 | 5.1 | 100 | 35.5 | 5.1 | 67.8 | 52.4 |
| Phenol | 65.4 | 1.6 | | 4.6 | 94.9 | | | 94.9 | 19.3 | 28.2 |
| PMC | | 0.7 | | 2.0 | | | | | 12.8 | 19.4 |

Conversion of phenol = 30%
(streams 1.14)
Production PMC = 4.3 Kg/hr
Specific energy consumption = 900 Kcal/Kg product

TABLE 4

| Stream | 1 | 2 | 3 | 5 | 7 | 8 | 9 | 10 | 11 | 14 |
|---|---|---|---|---|---|---|---|---|---|---|
| Kg/hr | 21.6 | 31.5 | 1.0 | 13.1 | 18.5 | 17.3 | 1.1 | 7.6 | 34.6 | 21.5 |
| % weight | | | | | | | | | | |
| $CH_3OH$ | | | | | 3.9 | | 64.5 | 3.9 | | |
| DMC | 59.0 | 97.1 | 100 | 93.1 | 96.1 | 100 | 35.5 | 96.1 | 68.0 | 52.8 |
| Phenol | 41.0 | 2.1 | | 5.0 | | | | | 21.4 | 31.3 |
| PMC | | 0.7 | | 1.7 | | | | | 10.5 | 15.9 |

Conversion of phenol = 24%
(streams 1.14)
Production PMC = 3.4 Kg/hr
Specific energy consumption = 1110 Kcal/Kg product

TABLE 5

| Stream | 1 | 2 | 3 | 5 | 7 | 8 | 9 | 10 | 11 | 14 |
|---|---|---|---|---|---|---|---|---|---|---|
| Kg/hr | 13.5 | 40.8 | 9.5 | 13.2 | 19.4 | 18.1 | 1.3 | 2.5 | 35.0 | 21.8 |
| % weight | | | | | | | | | | |
| $CH_3OH$ | | | | | 4.2 | | 64.5 | 4.2 | | |
| DMC | 34.6 | 94.6 | 100 | 93.2 | 89.1 | 92.8 | 35.5 | 89.1 | 67.9 | 52.6 |
| Phenol | 65.4 | 4.7 | | 4.8 | 6.7 | 7.2 | | 6.7 | 20.3 | 29.7 |
| PMC | | 0.6 | | 1.8 | | | | | 11.7 | 17.7 |

Conversion of phenol = 27%
(streams 1.14)
Production PMC = 3.8 Kg/hr
Specific energy consumption = 970 Kcal/Kg PMC

TABLE 6

| Stream | 1 | 2 | 3 | 5 | 7 | 8 | 9 | 10 | 11 | 14 |
|---|---|---|---|---|---|---|---|---|---|---|
| Kg/hr | 13.5 | 39.5 | 9.6 | 13.3 | 17.9 | 16.6 | 1.3 | 22.4 | 35.2 | 21.9 |
| % weight | | | | | | | | | | |
| $CH_3OH$ | | | | | 4.6 | | 64.5 | 4.6 | | |
| DMC | 34.6 | 97.7 | 100 | 93.2 | 95.4 | 100 | 35.4 | 95.4 | 68.0 | 52.7 |
| Phenol | 65.4 | 1.6 | | 4.8 | | | | | 20.1 | 29.4 |
| PMC | | 0.6 | | 1.9 | | | | | 11.8 | 17.9 |

Conversion of phenol = 27.3%
(streams 1.14)
Production PMC = 3.9 Kg/hr
Specific energy consumption = 1350 Kcal/Kg PMC

TABLE 7

| Stream | 1 | 2 | 3 | 5 | 13 | 8 | 9 | 12 | 11 | 14 |
|---|---|---|---|---|---|---|---|---|---|---|
| Kg/hr | 13.5 | 39.5 | 9.8 | 13.3 | 26.8 | 16.4 | 1.4 | 9.0 | 35.3 | 22.0 |
| % weight | | | | | | | | | | |
| $CH_3OH$ | | | | | 3.3 | | 64.5 | | | |
| DMC | 34.6 | 97.7 | 100 | 93.2 | 96.7 | 100 | 35.5 | 100 | 67.8 | 52.5 |
| Phenol | 65.4 | 1.6 | | 4.6 | | | | | 19.5 | 28.5 |
| PMC | | 0.7 | | 2.0 | | | | | 12.6 | 19.0 |

Conversion of phenol = 29%
(streams 1.14)
Production PMC = 4.2 Kg/hr
Specific energy consumption = 950 Kcal/Kg product

TABLE 8

| Stream | 1 | 2 | 3 | 5 | 13 | 8 | 9 | 12 | 11 | 14 |
|---|---|---|---|---|---|---|---|---|---|---|
| Kg/hr | 13.5 | 39.5 | 9.9 | 13.4 | 71.6 | 16.2 | 1.4 | 54.0 | 35.5 | 22.1 |
| % weight | | | | | | | | | | |
| $CH_3OH$ | | | | | 1.2 | | 64.5 | | | |
| DMC | 34.5 | 97.7 | 100 | 93.3 | 98.8 | 100 | 35.5 | 100 | 68.0 | 52.7 |
| Phenol | 65.4 | 1.6 | | 4.6 | | | | | 19.4 | 28.4 |
| PMC | | 0.7 | | 2.0 | | | | | 12.5 | 18.9 |

Conversion of phenol = 29%
(streams 1.14)
Production PMC = 4.2 Kg/hr
Specific energy consumption = 1940 Kcal/Kg product

We claim:

1. A continuous process for the preparation of phenyl methyl carbonate starting from phenol, dimethyl carbonate and a transesterification catalyst, which comprises:

(a) carrying out the process in a first distillation column consisting of a lower reactive section and an upper rectification section and in a second rectification column;

(b) feeding to the top of the reaction section of the first column a stream (I) containing phenol and optionally dimethylcarbonate in a ratio equal to or higher than 60/40 by weight and all of the catalyst;

feeding to the bottom of the reactive section of the same column a stream (II), comprising a stream or part of a stream (III) extracted from the bottom of the second column, containing dimethylcarbonate and optionally phenol in a ratio equal to or higher than 80/20 by weight;

the streams (I) and (II) being fed in such a quantity that the ratio between the total moles of dimethylcarbonate and phenol fed ranges from 2:1 and 10:1;

feeding to the top of the rectification section of the first column a stream (IV) which consists of the reflux of the column, having the composition of a stream (v) taken from the top of the column itself and fed to the second column, in such a quantity that the weight ratio of the reflexed liquid (stream IV) to the distillate (stream V) is within the range of 0.2–0.8;

c) extracting from the bottom of the reactive section of the first column a stream (VI) essentially containing all the non-reacted phenol, phenyl methyl carbonate and any possible diphenylcarbonate produced, the transesterification catalyst and a fraction of the dimethyl carbonate fed so that the molar ratio in this stream between the dimethylcarbonate and the phenol is between 0.5 and 5;

extracting from the top of the rectification section of the first column, a stream V, essentially containing dimethylcarbonate and all or basically all of the methanol produced by the reaction;

d) feeding to an intermediate section of the second column a stream (V) extracted from the top of the first column;

e) extracting from the top of the second column a stream (VII) containing all or practically all of the methanol fed to the second column and dimethyl carbonate in a ratio of more than 50% by weight;

extracting from the bottom of the second column a stream (III) essentially consisting of the remaining dimethylcarbonate;

f) recycling said stream III or part of it to the bottom of the first column.

2. The process according to claim 1, wherein the feed to the intermediate section of the second column consists of a stream (IX) taken from the top of the first column and the feed to the top of the rectification section of the first column of a stream (VIII) which forms the reflux of the column and is separated from stream (III), streams (VIII) and (IX) being fed in such a quantity that the weight ratio between the reflexed liquid (stream VIII) and the distillate (streams IX–VIII) is within the range of 0.2–0.8.

3. The process according to claim 1 or 2, wherein the reactive distillation section of the first column comprises at least 3 theoretical distillation steps and the rectification section comprises at least 3 theoretical distillation steps.

4. The process according to claim 1, wherein stream (V) or stream (IX) contains phenol at a concentration of less than 2% by weight.

5. The process according to claim 1, wherein the concentration of methanol in stream (V) or in stream (IX) ranges from 1 to 5% by weight.

6. The process according to claim 1, wherein the operating pressure of the first column, measured at the top of the column, ranges from 3 to 10 absolute bars.

7. The process according to claim 1, wherein the temperature measured at the top of the first column ranges from 100° and 210° C. and the temperature at the bottom of the reactive section ranges from 250° and 150° C.

8. The process according to claim 1, wherein the difference between the temperature of the bottom and the temperature of the feeding zone of stream (I) is not higher than 20° C.

9. The process according to claim 1, wherein the second column contains at least 10 theoretical distillation steps and is fed in such a way that the theoretical steps present above and below the feeding are arranged in a ratio ranging from 1/3 to 3/1.

10. The process according to claim 1, wherein the second column operates at a pressure, measured at the top, ranging from 1 to 10 absolute bars and a temperatures at the top and bottom ranging from 65° and 135° C. and from 90° to 180° C. respectively.

11. The process according to claim 1, wherein the reaction is carried out in the presence of a catalyst based on alkoxides and aryl oxides of titanium and said catalyst is present in a molar quantity ranging from 0.1 to 10% with respect to the total phenol fed.

12. The process according to claim 1, wherein stream (VI) or part of it, extracted from the bottom of the reactive section of the first column is subjected to adiabatic flash by pressure reduction in a flash chamber and the vaporized stream thus obtained, extracted from the top of the flash chamber, is fed to the bottom of the reactive section of the first column to form, together with stream (III) or part of it and optionally fresh dimethyl carbonate, stream (II).

13. The process according to claim 12, wherein the flash chamber operates at atmospheric pressure and the flash temperature ranges from 130° and 170° C.

14. The process according to claim 12, wherein the vaporized stream taken from the top of the flash chamber is in a quantity equal to a fraction by weight of the feeding of the chamber itself ranging from 20 to 40%.

15. The process according to claim 12, wherein the stream taken from the top of the flash chamber contains dimethyl carbonate and phenol in a ratio equal to or higher that 80/20 by weight.

16. The process according to claim 12, wherein the stream taken from the bottom of the flash chamber contains a ratio phenol/dimethylcarbonate higher than that present in the stream fed, as well as most of the product formed and all of the catalyst.

17. The process according to claim 1, wherein the molar ratio of dimethylcarbonate to phenol of streams (I) and (II) ranges from 3:1 to 6:1, and wherein the molar ratio of dimethylcarbonate to phenol in step (c) ranges from 1 to 5.

18. The process according to claim 2, wherein the weight ratio of refluxed liquid to distillate ranges from 0.2 to 0.8.

19. The process according to claim 3, wherein the number of distillation steps ranges from 5 to 25.

20. The process according to claim 6, wherein said operating pressure ranges from 4 to 8 absolute bars.

21. The process according to claim 7, wherein the respective top and bottom temperatures range from 140° to 180° C. and 220° to 180° C. respectively.

22. The process according to claim 9, wherein the number of theoretical distillation steps ranges from 20 to 50 and wherein said ratio of distillation steps ranges from 1/1 to 1/3.

23. The process according to claim 11, wherein said catalyst is titanium tetraphenate, and the molar amount of said catalyst ranges from 0.2 to 2%.

* * * * *